US006862542B2

(12) United States Patent
Lockhart et al.

(10) Patent No.: US 6,862,542 B2
(45) Date of Patent: Mar. 1, 2005

(54) ERYTHEMA MEASURING DEVICE (75) Inventors: Peter Lockhart, Charlotte, NC (US); Robert Splinter, Huntersville, NC (US); Matthew J. Davis, Concord, NC (US)

(73) Assignee: Charlotte-Mecklenburg Hospital, Charlotte, NC (US)

( * ) Notice: Subject to any disclaimer, the term of this patent is extended or adjusted under 35 U.S.C. 154(b) by 547 days.

(21) Appl. No.: 10/053,103

(22) Filed: Jan. 17, 2002

(65) Prior Publication Data

US 2003/0135098 A1 Jul. 17, 2003

(51) Int. Cl.[7] .............................. G06F 19/00; A61B 5/00
(52) U.S. Cl. ......................... 702/76; 600/310; 600/473; 600/476
(58) Field of Search ............................. 702/28, 29, 76; 600/310, 473, 476

(56) References Cited

U.S. PATENT DOCUMENTS

| 5,818,587 | A | * | 10/1998 | Devaraj et al. ............. 356/477 |
| 6,045,502 | A | * | 4/2000 | Eppstein et al. ............ 600/306 |
| 6,070,092 | A | * | 5/2000 | Kazama et al. ............ 600/310 |
| 6,081,612 | A | * | 6/2000 | Gutkowicz-Krusin et al. .......................... 382/128 |
| 6,230,046 | B1 | * | 5/2001 | Crane et al. ................ 600/476 |
| 6,522,911 | B1 | * | 2/2003 | Toida et al. ................ 600/473 |
| 6,587,711 | B1 | * | 7/2003 | Alfano et al. ............... 600/476 |
| 6,631,288 | B1 | * | 10/2003 | Bain et al. .................. 600/476 |
| 2002/0084417 | A1 | * | 7/2002 | Khalil et al. ............. 250/341.8 |
| 2003/0018271 | A1 | * | 1/2003 | Kimble ...................... 600/473 |
| 2003/0109773 | A1 | * | 6/2003 | Samuels et al. ............ 600/315 |
| 2004/0039379 | A1 | * | 2/2004 | Viator et al. ................... 606/9 |
| 2004/0073374 | A1 | * | 4/2004 | Lockhart et al. ............. 702/19 |
| 2004/0167502 | A1 | * | 8/2004 | Weckwerth et al. ........... 606/9 |

* cited by examiner

Primary Examiner—Patrick Assouad
(74) Attorney, Agent, or Firm—Bond, Schoeneck & King, PLLC (57) ABSTRACT The present invention provides an erythema meter comprising a light guide that carries light of two specific wavelengths (probing and reference) at two distinct frequencies that are generated and modulated by a either a single or multiple source(s), a photodetector mounted in the tip of the guide that receives light reflected from the surface being examined, and circuitry electrically coupled to the guide for processing the light data, and determining the level of erythema present on the examined surface. The probing and reference wavelengths are delivered in sinusoidal or amplitude modulated fashion, thereby permitting electronic filtering of the received data. A calculating circuit determines the quotient of the two wavelengths after having been reflected off of a surface, such as mucosal or dermal surfaces, which is representative of the severity of erythema present in the surface.

6 Claims, 10 Drawing Sheets

ERYTHEMA MEASURING DEVICE

BACKGROUND OF THE INVENTION

1. Field of Invention

The present invention relates generally to meters for detecting erythema, and more particularly to such meters that utilize two different wavelengths of light to measure the erythema.

2. Description of Prior Art

Erythema is an abnormal redness or inflammation of a mucosal (e.g., mouth) or dermal (i.e., skin) surface caused by dilation of superficial capillaries. It can result from many different causes, including diseases of the mucosa and skin, and some systematic diseases. In more severe forms, it can cover large areas of the body and have a component of ulceration, either solitary or widespread. For example, erythema multiforme is a reddening, swelling, and possibly blistering of a dermal surface that comes in multiple forms. It is an allergic (hypersensitivity) inflammatory reaction to a stimulus (allergen). This type of erythema has innumerable causes that can be loosely categorized as infections, medications, blood vessel disease, and neoplasms. Most cases are thought to be caused by herpes virus infections. Erythema is also common during and following cancer chemotherapy and radiotherapy, and can result in ulceration, severe pain, infection, and interference with nutritional intake, sleep, and speech A more common, almost universal disease affecting mankind, and which has an erythematous component is periodontal disease. Periodontitis is a term used to describe an inflammatory disease affecting the tissues surrounding and supporting the teeth. In mild cases (i.e., gingivitis), only the soft gum tissue is affected. Erythema, along with a swelling of the gums, is caused by an underlying bacterial infection. If not detected early, this condition can progress to periodontitis and result in active destruction of the supporting bone tissues around the teeth, resulting in their loss.

The determination of the degree of erythema has always been problematic for researchers who develop and clinicians who use medications to prevent or decrease erythema in these patients. Current methods for detecting erythema on mucosal and skin are highly subjective, not re-produceable, and often do not detect disease in an early stage when treatment and preventive strategies are most effective. In addition, these methods do not provide a baseline for a particular patient, and are dependent upon patient cooperation, examiner direct line of sight, and the available lighting.

3. Objects and Advantages

It is therefore a principal object and advantage of the present invention to provide a device that can accurately measure the erythema of a mucosal or dermal surface in a quantitative manner.

It is another object and advantaged of the present invention to provide an erythema measuring device that permits early detection of a disease process or disorder, serve as a baseline for a given patient, provide for early intervention in situations where the process can be altered, and provide a research tool for studies concerning disorders where skin and mucosal surfaces are altered by changes in the blood supply.

Other objects and advantages of the present invention will in part be obvious, and in part appear hereinafter.

SUMMARY OF THE INVENTION

In accordance with the foregoing objects and advantages, the present invention provides an erythema meter comprising a light guide that carries light of two specific wavelengths (probing and reference) generated by a either a single or multiple source(s), a photodetector mounted in the tip of the guide that receives light reflected from the surface being examined, and circuitry electrically coupled to the guide for processing the light data, and determining the level of erythema present on the examined surface. The probing and reference wavelengths are delivered in sinusoidal or amplitude modulated fashion, thereby permitting electronic filtering of the received data. The electronic signal processing with a phase locked loop is similar to AM radio tuning, making operation of the meter independent of ambient light and impervious to operating conditions.

In operation, the two wavelengths (i.e., green and red light at 5.21 KHz and 2.31 KHz, respectively) are directed perpendicularly to, and reflected off of the mucosal/dermal surface. The two wavelengths are generated and modulated in intensity and at frequencies separated far enough apart that they will not be detected by the phase sensitive detection mechanism tuned to the individual light source frequencies. One wavelength is used as the reference measurement and is selected so that it will interact with the tissue irrespective of blood content, while the other wavelength is selected in a spectral range of preferential absorption in blood, both oxygenated and reduced. The ratio of the reflected signals of the two wavelength provides a measure of severity of erythema.

BRIEF DESCRIPTION OF THE DRAWINGS

The present invention will be better understood and more fully appreciated by reading the following Detailed Description in conjunction with the accompanying drawings, in which.

DETAILED DESCRIPTION

Figure 1:
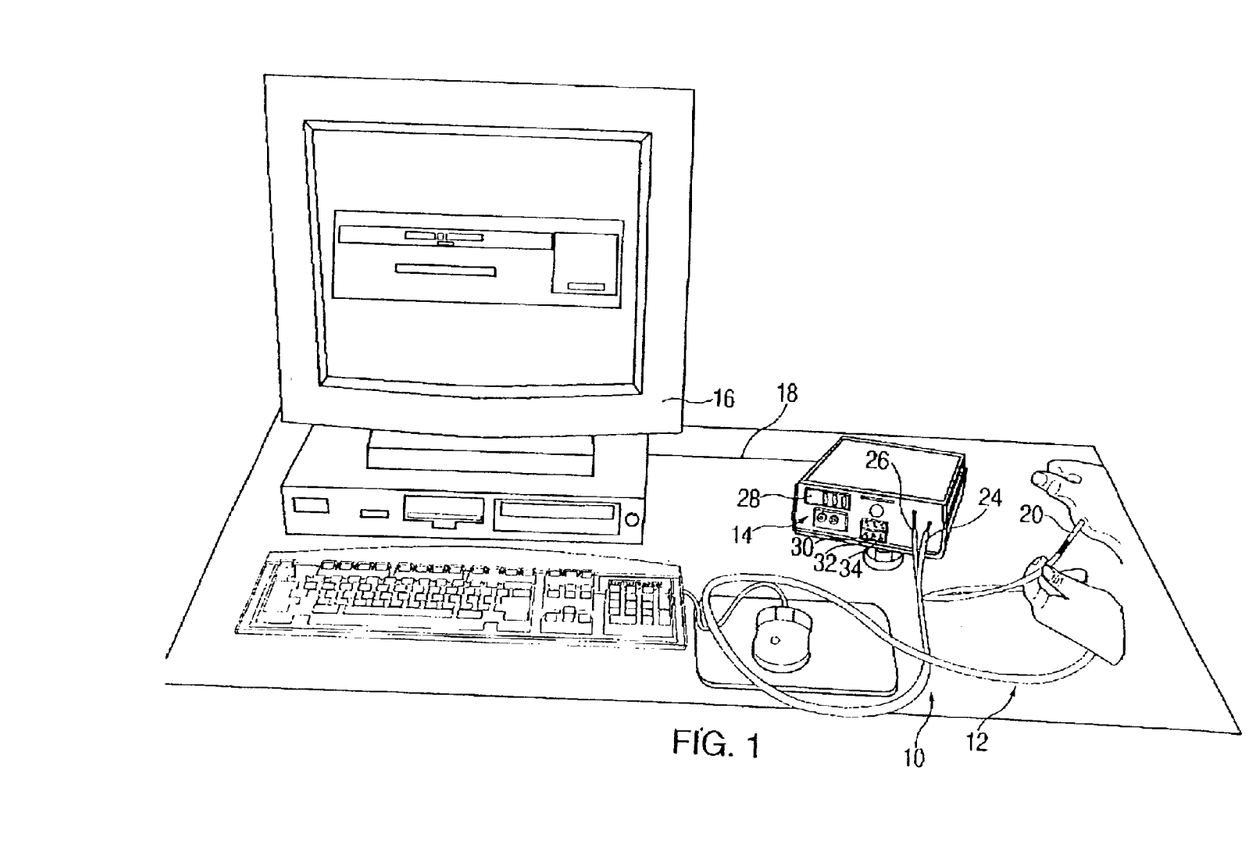
FIG. 1 is a perspective view of the present invention.
Figure 2:
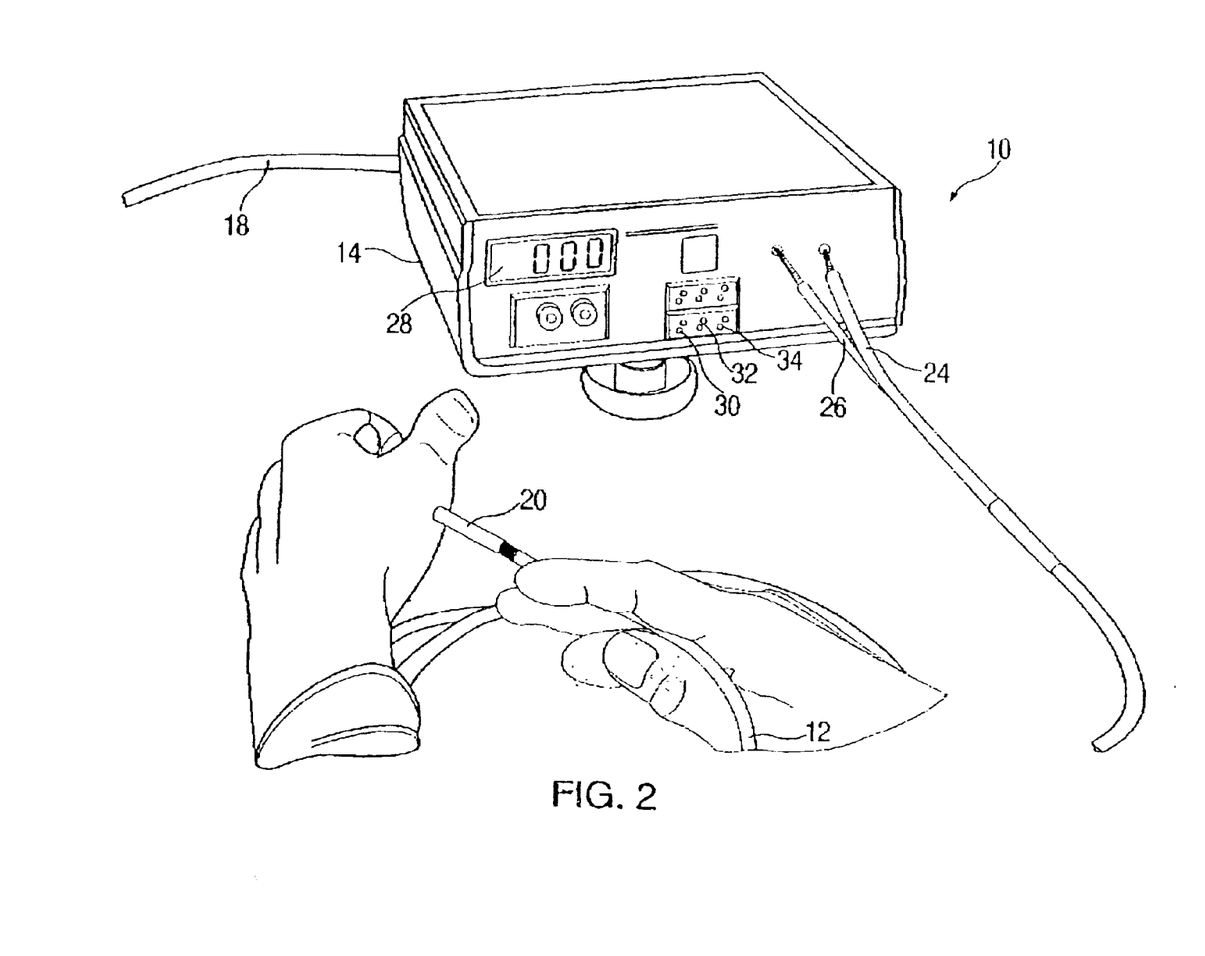
FIG. 2 is an enlarged perspective view of the light guide and meter of the present invention.
Figure 3:
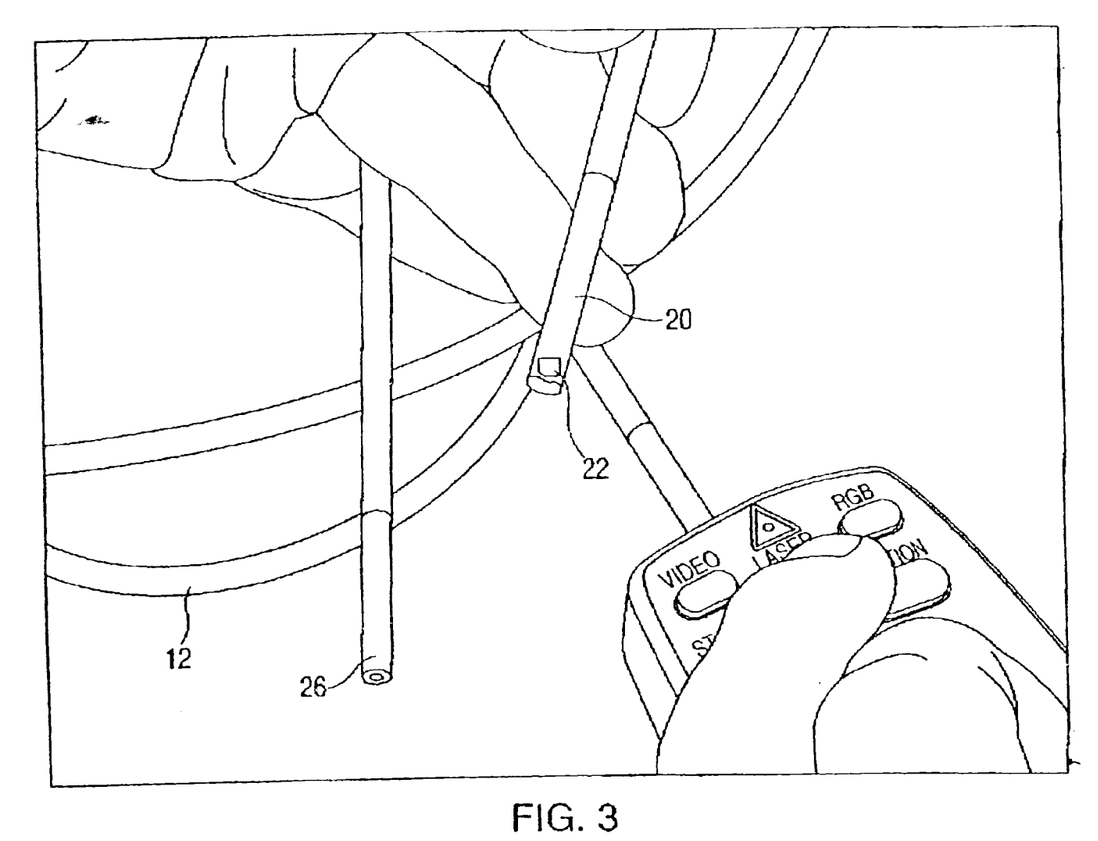
FIG. 3 is an enlarged perspective view of the spilt tip of the light guide.

Referring now to the drawings, wherein like reference numerals refer to like parts throughout, there is seen in FIGS. 1–3 a system for measuring erythema, designated generally by reference numeral 10, comprising a light guide 12, a generator/meter box 14 electrically coupled to light guide 12, and, optionally, a computer 16 electrically connected via a standard RS 232 protocol cable 18 to generator/meter 14 for data logging.

Light guide 12 comprises a probe 20, the tip of which contains a photo transistor 22, such as the Type OP800SL silicon photo transistor manufactured by Optek Technology, Inc. An optical fiber (or other light transmitting/carrying device) extends through guide 12 and probe 20, and is split into two strands 24, 26 at its rearward position. Strand 24 carries the light from generator/meter box 14 to probe 20. Strand 24 carries the received light and switches it to strand 26 which ultimately carries the reflected light collected by photo transistor 22 back to generator/meter box 14 for processing.

Generator/meter box 14 houses a wave generator, as will be explained in greater detail hereinafter, for delivering pulses of energy to a light generator, such as a laser or LED, which in turn delivers at least two wavelengths of light (referred to on the drawings as "Red" and "Green") to optical strand 24; a display, such as a LCD, 28 for displaying the erythema value; standard calibration and adjustment setting dials 30; standard wavelength selection buttons 32; number of wavelengths to be generated selector keys 34, as well as the circuitry for delivering, filtering, and processing the received light data, as will be explained in greater detail hereinafter. The at least two frequencies are selected such that modulation thereof produces low noise, in addition to the harmonics of the modulated frequencies not overlapping, and at frequencies that are not so high to prevent LEDs and detectors from being able to effectively process them (i.e., it is the modulation of the two wavelengths at respective, predetermined frequencies that permits the circuitry to discern one signal from the other and permits the passing of two (or more if desired) wavelengths through a common wave guide). Preferably, one of the frequencies is selected as a reference measurement and will interact with tissue irrespective of blood content, while the other frequency is selected in a spectral range of preferential absorption in blood, both oxygenated and reduced.

Figure 4:
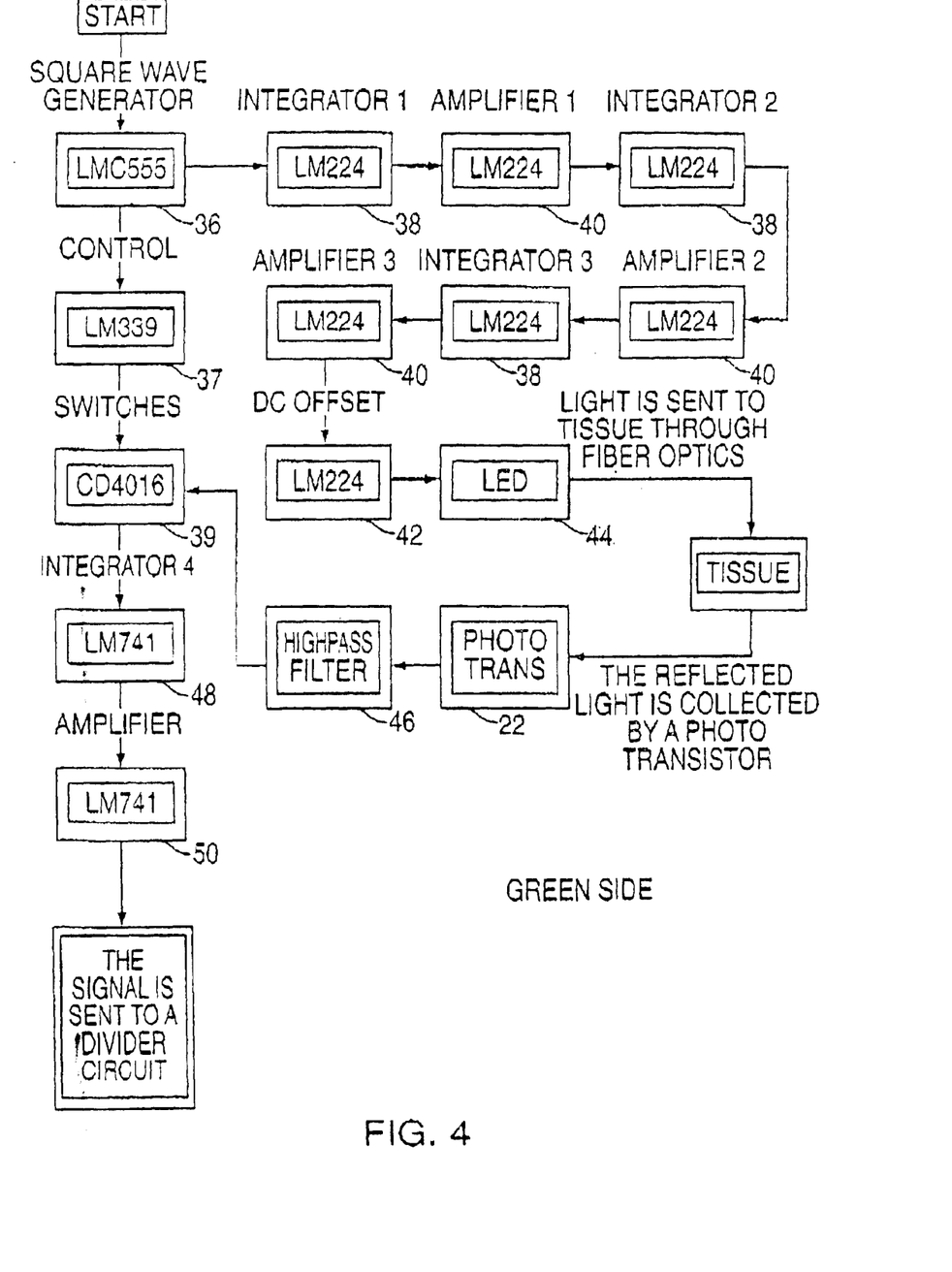
FIG. 4 is a medium level flow chart of the first (e.g., green) wavelength circuitry.
Figure 5:
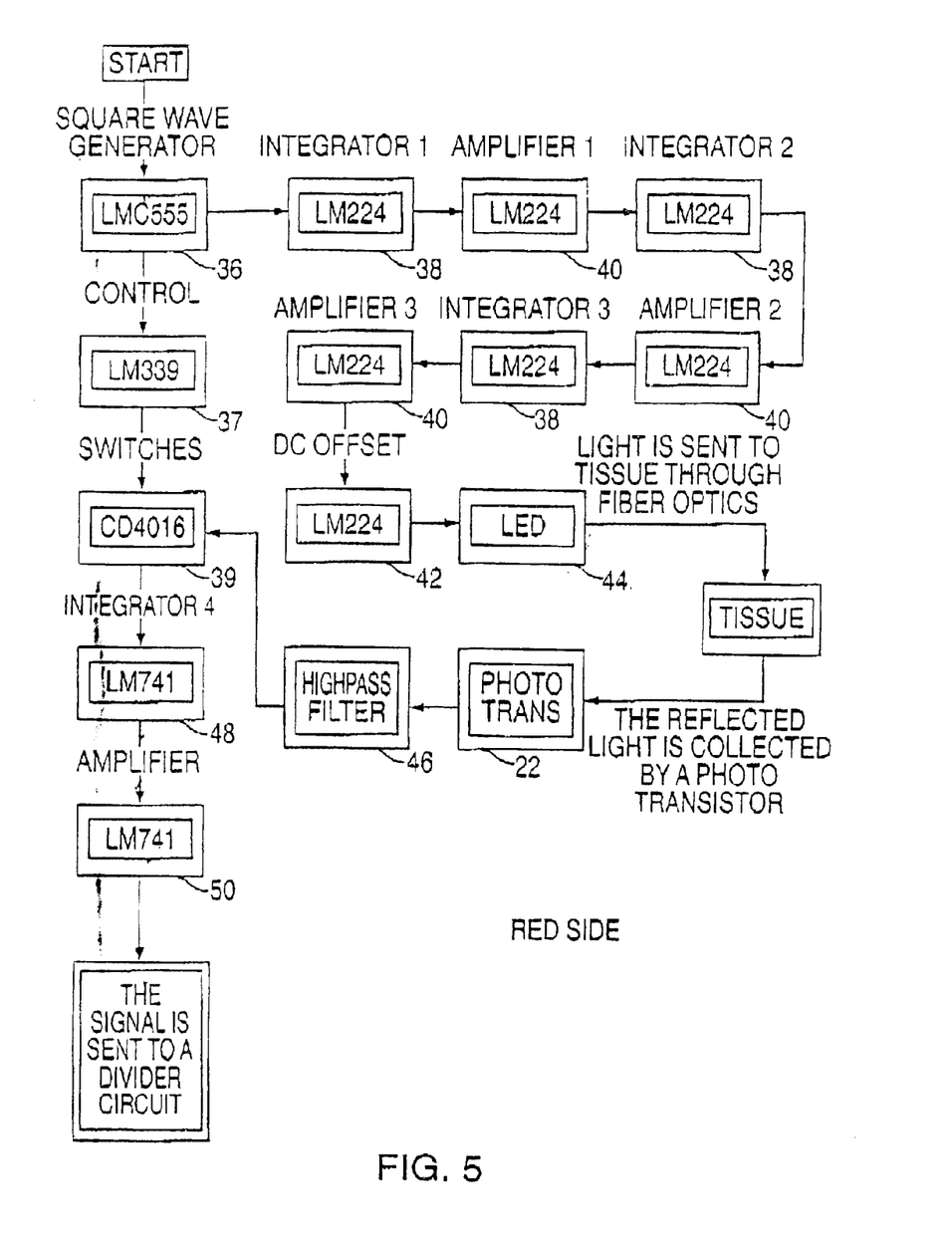
FIG. 5 is a medium level flow chart of the second (e.g., red) wavelength circuitry.

With reference to FIGS. 4–9, the layout of the circuitry for performing the erythema measurement is seen in various levels of detail. Referring to FIGS. 4 and 5, both wavelengths are generated with a standard squarewave generator (clock) 36, and modulated (pulsed) at respective predetermined frequencies. The modulated signals from squarewave generator 36 are sent to a comparator circuit 33 (see FIGS. 7a and 8a) comprised of several series of integrators 38 and amplifiers 40, such as the LM224 low power quad operational amplifier manufactured by National Semiconductor, with the signal ultimately passing through a DC offset 42 to account for the integrators' treatment of the amplifier signals as constants. Meanwhile, the control wavelengths are modulated at the respective, identical frequencies (i.e., the same modulated frequencies that were transmitted to comparator circuit 33) are sent from generator 36 through a comparator 37 and rectifier 39 for control purposes, prior to it passing on to a divider circuit, as will be explained in greater detail hereinafter for use in calculating the level of erythema.

The comparator 33 will convert the squarewave to a sine wave and trigger an LED (or laser diode) 44 at a particular frequency (the two wavelengths are modulated at two distinct frequencies, as described herinabove). LED 44 will transmit light through fiber strand 24 and out of probe 20 where the examiner can direct the light toward the tissue being examined. Light reflecting off of the tissue will then be received by photo transistor 22 and carried back through fiber strands 24 and 26. The light signal is then passed through a highpass filter 46 which electronically filters the signal by means of lock-in amplifiers that lock in at the respective pulsing frequencies and measure the reflected light intensity (radiance) only at those frequencies. This filtering is advantageous in the environment of erythema detection due to its sensitive signal to noise ratio, sensitive detection capability and ability to adapt the instrumentation for variations in the examination environment, as well as patient specific pathological conditions.

Figure 6:
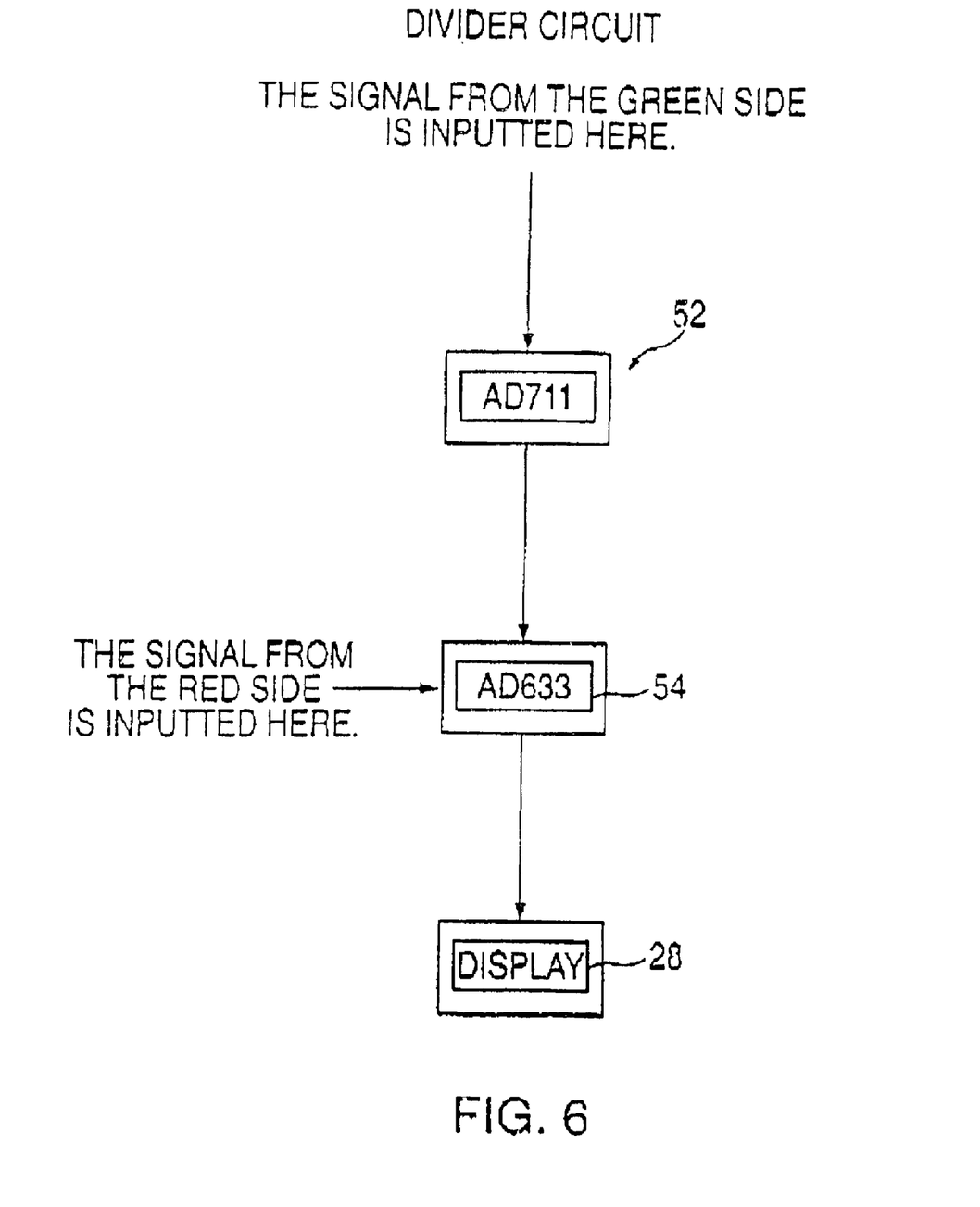
FIG. 6 is a medium level flow chart of the divider circuitry.
Figure 7A:
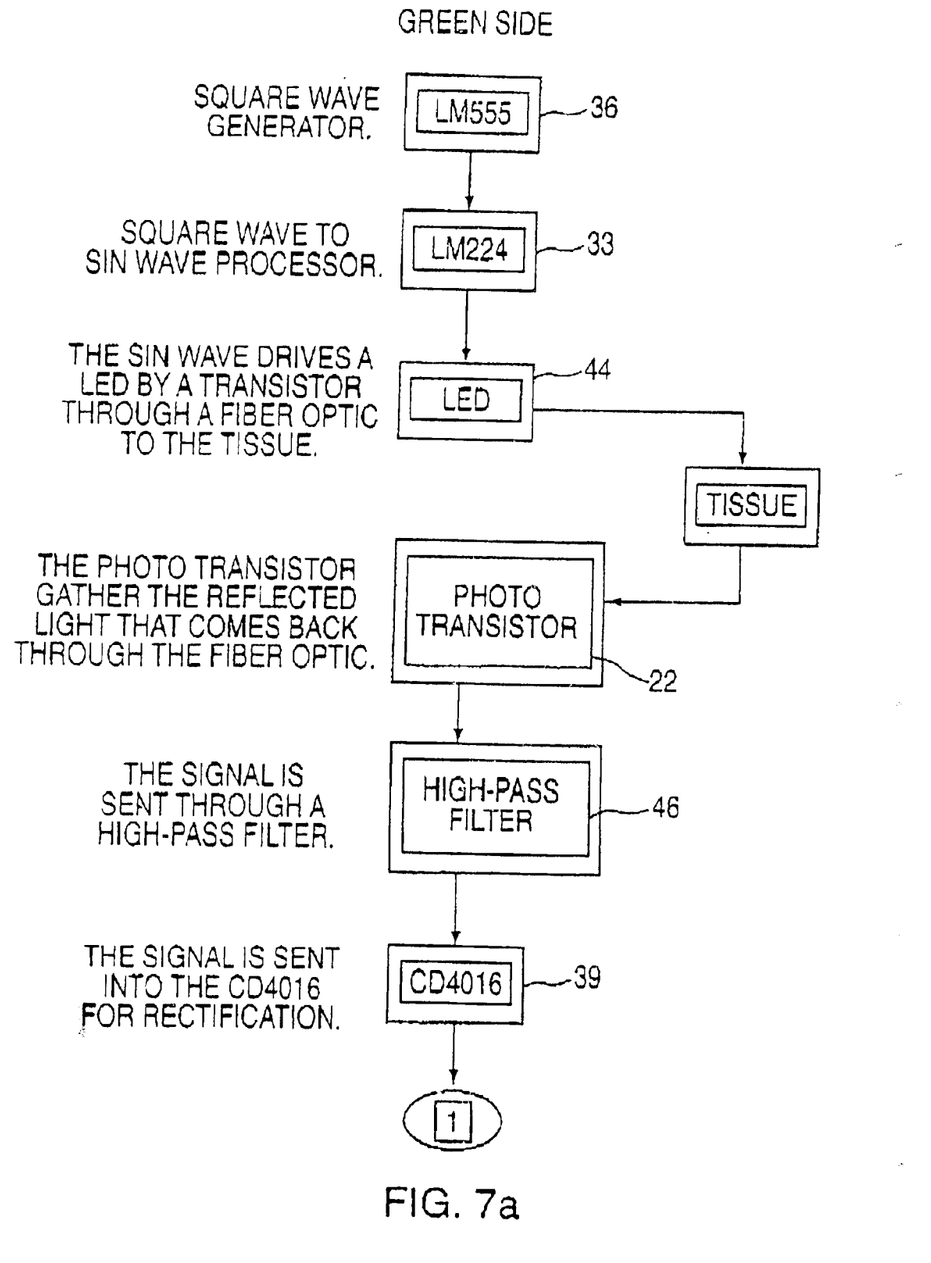
FIGS. 7*a* and 7*b* are high level flow charts of the circuitry shown in FIGS. 4 and 6, respectively.
Figure 7B:
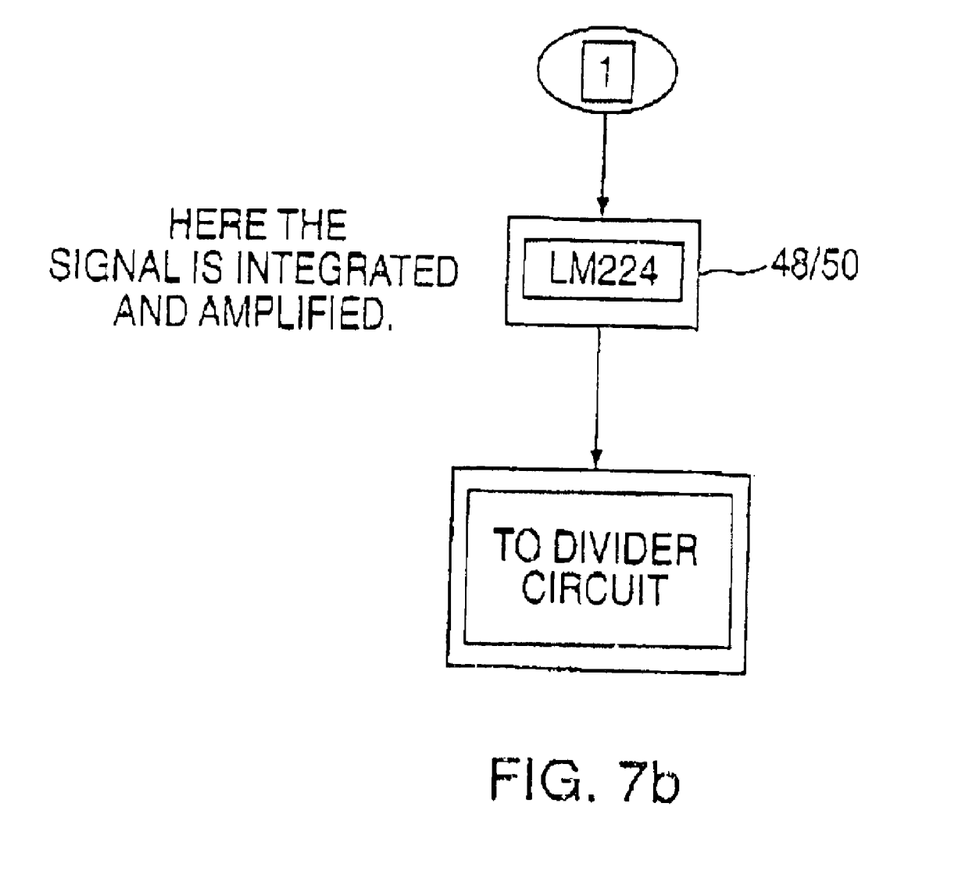
Figure 8A:
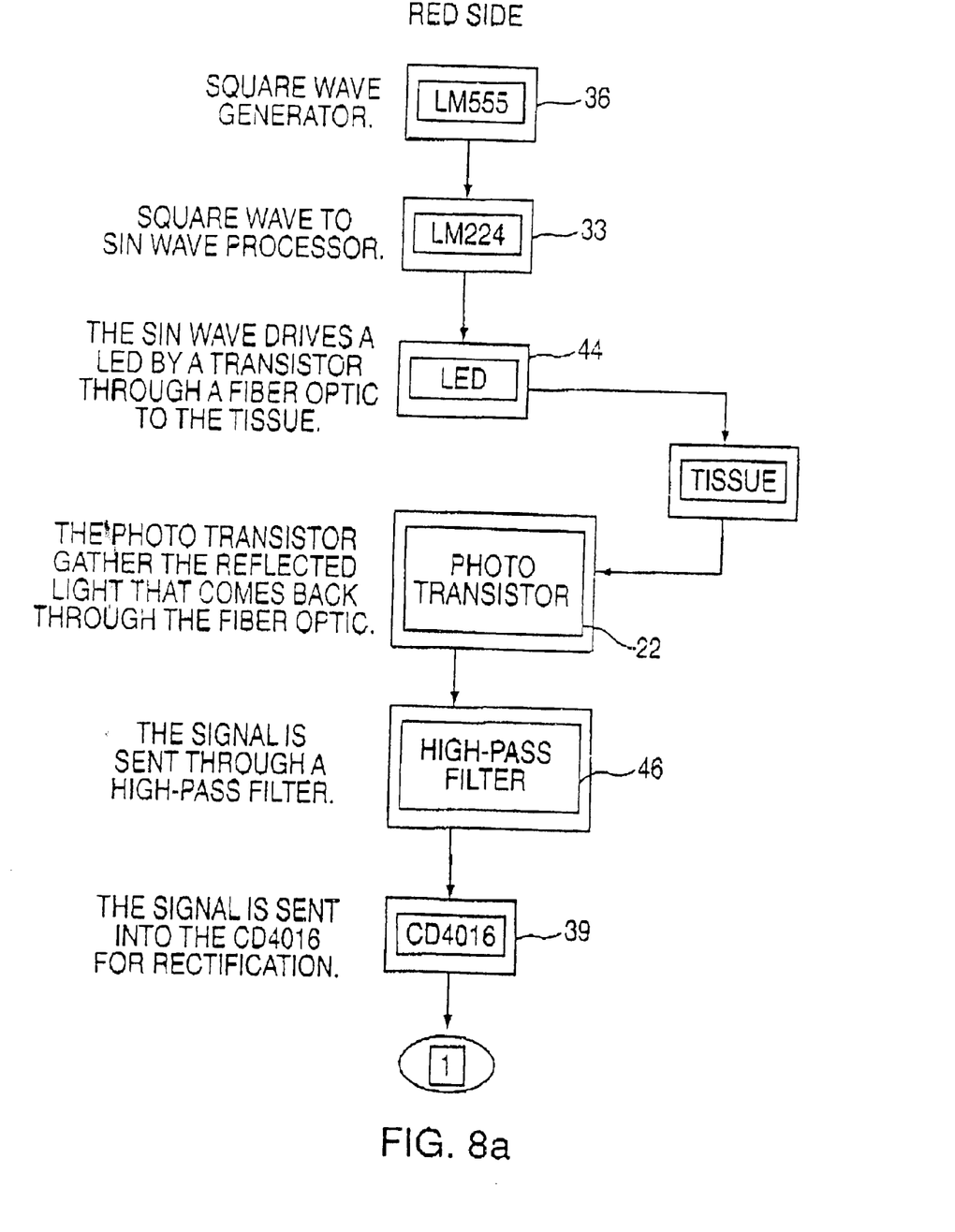
FIGS. 8*a* and 8*b* are high level flow charts of the circuitry shown in FIGS. 5 and 6, respectively.
Figure 8B:
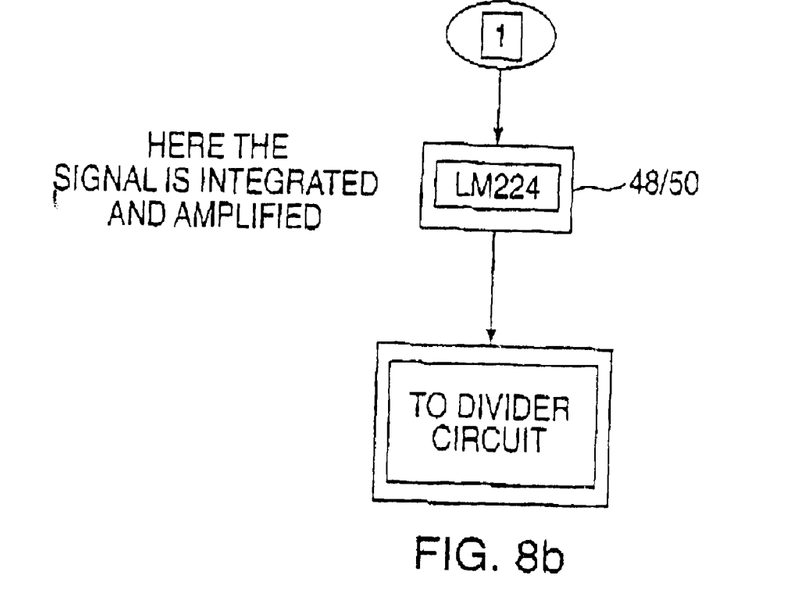
Figure 9:
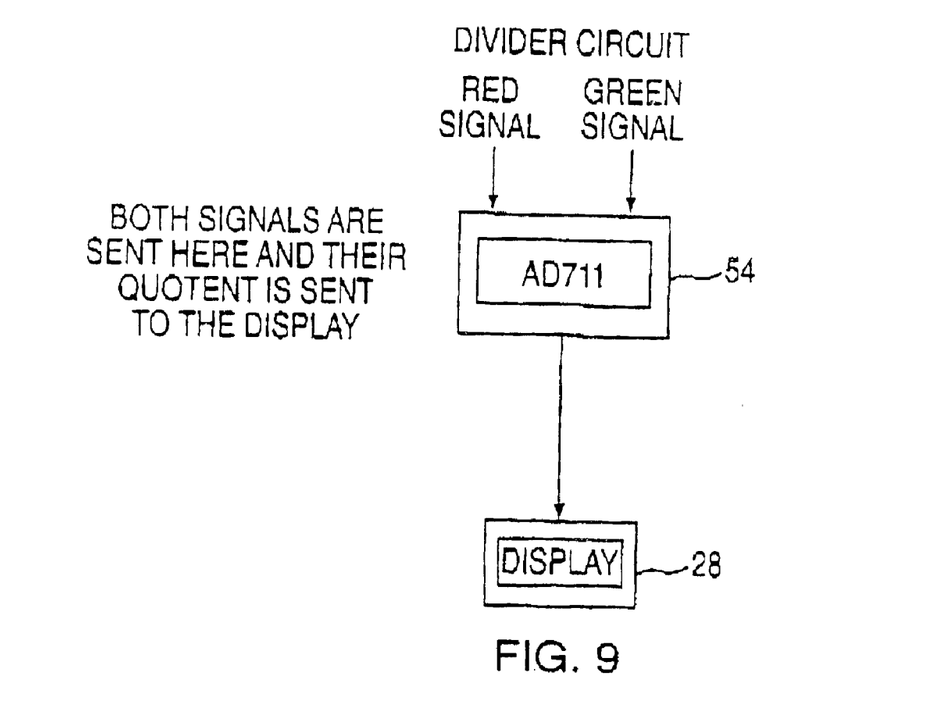
FIG. 9 is a high level flow chart of the display portion of the circuitry.

Once filtered, the signal is sent through rectifier 39 where it is synchronized with the control wavelength modulated at the same frequency. The signal resulting from the combination of the control wavelength and filtered signal is then sent to a comparator comprising an integrator 48 and amplifier 50, such as the LM741 operational amplifier manufactured by National Semiconductor, and is then passed on to a divider circuit 52 comprising an amplifier 53, such as the AD711 operational amplifier manufactured by Analog Devices, and a multiplier 55, such as AD633 analog multiplier manufactured by Analog Devices. Divider circuit 52 takes the reflected radiance at the respective illuminating wavelengths and divides them by the reference or control wavelength radiance for healthy tissue, the quotient providing a numerical indication of the degree of erythema. The numerical representation of the degree of erythema is then sent through an analog to digital converter 54 and numerically displayed on display 28.

What is claimed is:

1. A system for measuring erythema, comprising:
   a. a light guide having first and second opposite ends;
   b. a waveform generator for generating at least first and second signals, and modulating said first and second signals at first and second predetermined frequencies, respectively;
   c. a light source electrically interconnected to said waveform generator for transmitting light to a surface at said first and second frequencies;
   d. a photo transistor mounted in said light guide at said second end for receiving reflected light and generating a second signal;
   e. a calculator circuit for determining a level of erythema based on said second signal; and
   f. a display unit electrically interconnected to said calculator circuit for displaying said level of erythema.

2. An erythema measuring device, comprising:
   a. a waveform generator for generating first and second waveforms;
   b. a light guide interconnected to said waveform generator for guiding and transmitting light to a surface at first and second frequencies corresponding to said first and second waveforms, respectively;
   c. a photo transistor connected to said light guide for receiving light reflected from said surface;
   d. an electronic highpass filter for filtering said reflected light received by said photo transistor;
   e. an analog to digital converter electrically coupled to said filter; and
   f. a display unit electrically coupled to said analog to digital converter.

3. A method for measuring erythema present on a surface, comprising the steps of:
   a. transmitting first and second wavelengths of light towards said surface;
   b. receiving said first and second wavelengths of light after they have been reflected off of said surface;
   c. electronically filtering said first and second wavelengths of reflected light;
   d. calculating a level of erythema based on said filtered first and second wavelengths of light; and
   e. displaying said level of erythema.

4. An erythema measuring device, comprising:
 a. means for generating first and second waveforms;
 b. means for transmitting light to a surface at first and second frequencies corresponding to said first and second waveforms, respectively;
 c. means for receiving light reflected from said surface;
 d. means for filtering said reflected light received by said light receiving means;
 e. an analog to digital converter electrically coupled to said filtering means; and
 f. a display unit electrically coupled to said analog to digital converter.

5. An erythema measuring device, comprising:
 a. means for generating first and second waveforms and modulating said first and second waveforms at first and second predetermined frequencies, respectively;
 b. means for transmitting light to a surface at said first and second frequencies;
 c. means for receiving light reflected from said surface;
 d. means for calculating a level of erythema based on said light reflected from said surface; and
 e. a display unit for displaying said level of erythema.

6. A method for measuring erythema present on a surface, comprising the steps of:
 a. generating first and second wavelengths and modulating them at first and second frequencies, respectively;
 b. transmitting said first and second wavelengths of light towards said surface;
 c. receiving said first and second wavelengths of light after they have been reflected off of said surface;
 d. calculating a level of erythema based on said reflected first and second wavelengths of light; and
 e. displaying said level of erythema.

* * * * *